(12) United States Patent
Melik et al.

(10) Patent No.: US 6,794,023 B1
(45) Date of Patent: Sep. 21, 2004

(54) POLYMER PRODUCTS COMPRISING SOFT AND ELASTIC BIODEGRADABLE POLYHYDROXYALKANOATE COPOLYMER COMPOSITIONS AND METHODS OF PREPARING SUCH POLYMER PRODUCTS

(75) Inventors: David Harry Melik, Cincinnati, OH (US); Isao Noda, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/111,497

(22) PCT Filed: Oct. 27, 2000

(86) PCT No.: PCT/US00/29884
§ 371 (c)(1),
(2), (4) Date: Apr. 25, 2002

(87) PCT Pub. No.: WO01/30892
PCT Pub. Date: May 3, 2001

Related U.S. Application Data

(60) Provisional application No. 60/161,969, filed on Oct. 28, 1999.

(51) Int. Cl.$^7$ .............................. B32B 7/02; C08F 20/00; C08G 63/02
(52) U.S. Cl. ..................... 428/221; 428/364; 428/365; 528/361; 525/444; 264/210.1
(58) Field of Search .......................... 528/361; 525/444, 525/450, 437; 428/221, 364, 365, 362; 264/210.1, 210.7

(56) References Cited

U.S. PATENT DOCUMENTS

| | | |
|---|---|---|
| 4,116,892 A | 9/1978 | Schwarz |
| 4,393,167 A | 7/1983 | Holmes et al. |
| 4,427,614 A | 1/1984 | Barham et al. |
| 4,537,738 A | 8/1985 | Holmes |
| 4,880,592 A | 11/1989 | Martini et al. |
| 5,296,184 A | 3/1994 | Wu et al. |
| 5,498,692 A | 3/1996 | Noda |
| 5,536,564 A | 7/1996 | Noda |
| 5,602,227 A | 2/1997 | Noda |
| 5,618,855 A | 4/1997 | Noda |
| 5,685,756 A | 11/1997 | Noda |
| 5,942,597 A | 8/1999 | Noda et al. |
| RE36,548 E | 2/2000 | Noda |

FOREIGN PATENT DOCUMENTS

| | | |
|---|---|---|
| EP | 0 736 563 A1 | 10/1996 |
| EP | 0 849 311 A2 | 6/1998 |
| EP | 0 723 983 B1 | 8/2001 |
| JP | 10-147653 A | 6/1998 |
| WO | WO 92/04412 A1 | 3/1992 |
| WO | WO 95/20614 A1 | 8/1995 |
| WO | WO 95/20615 A1 | 8/1995 |
| WO | WO 97/22459 A1 | 6/1997 |
| WO | WO 00/37544 A1 | 6/2000 |
| WO | WO 01/30893 A1 | 5/2001 |

OTHER PUBLICATIONS

Kusaka, Satoshi, et al., "Properties and biodegradability of ultra–high–molecular–weight poly[(R)3–hydroxybutyrate] produced by a recombinant *Escherichia coli*", International Journal of Biological Macromolecules, 25 (1999) pp. 87–94.

K.D. Gagnon et al., "Elastomers Based On Polyesters Produced By the Bacterium *Pseudomonas oleovorans*", Macromolecules, vol. 25, pp. 3723–3728, 1992.

Kusaka et al., Microbial Synthesis And Physical Properties Of Ultra–High–Molecular–Weight Poly [(R)3–hydroxybutyrate], Pure Appl. Chem., 834(2):319–335, 1998.

Yamamoto et al., "The Effect of Drawing and Annealing Conditions on the Structure and Properties of Bacterial Poly(3–hydroxybutyrate–co–3 hydroxyvalerate) Fibers", Intern. Polymer Processing XII, 1997, 1:29–37.

*Primary Examiner*—Samuel A. Acquah
(74) *Attorney, Agent, or Firm*—Leonard W. Lewis

(57) ABSTRACT

Soft and elastic polymer products are obtained by stretching a composition comprising a biodegradable polyhydroxyalkanrate copolymer comprising at least two randomly repeating monomer units. The first randomly repeating monomer unit has the structure (I), wherein $R^1$ is H, or C1 or C2 alkyl, and n is 1 or 2. The second randomly repeating monomer unit has the structure (II), wherein R2 is a C3–C19 alkyl or C3–C19 alkenyl. At least about 70 mole % of the copolymer comprises randomly repeating monomer units having the structure of the first randomly repeating monomer unit (I). The products exhibit advantageous combinations of softness and elasticity while maintaining strength.

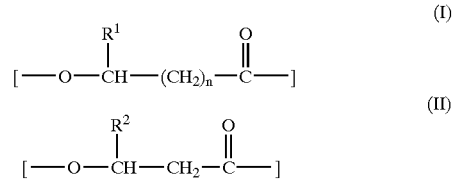

21 Claims, No Drawings

POLYMER PRODUCTS COMPRISING SOFT AND ELASTIC BIODEGRADABLE POLYHYDROXYALKANOATE COPOLYMER COMPOSITIONS AND METHODS OF PREPARING SUCH POLYMER PRODUCTS

This application claims the benefit of provisional application Ser. No. 60/161,969, filed Oct. 28, 1999.

FIELD OF THE INVENTION

The present invention is directed to polymer products, including, but not limited to, films, fibers, nonwovens, and sheets, obtained by stretching a composition comprising a biodegradable polyhydroxyalkanoate copolymer. The products exhibit a desirable combination of softness and elasticity while maintaining strength. The products are useful for various biodegradable articles including diaper topsheets, diaper backsheets, garbage bags, food wrap, disposable garments and the like.

BACKGROUND OF THE INVENTION

Biodegradable polymers and products formed from biodegradable polymers are becoming increasingly important in view of the desire to reduce the volume of solid waste materials generated by corders each year.

In the past, the biodegradability and physical properties of a variety of polyhydroxyalkanoates have been studied. Polyhydroxyalkanoates are polyester compounds produced by a variety of microorganisms, such as bacteria and algae. While polyhydroxyalkanoates have been of general interest because of their biodegradable nature, their actual use as a plastic material has been hampered by their thermal instability. For example, poly-3-hydroxybutyrate (PHB) is a natural energy-storage product of bacterial and algae, and is present in discrete granules within the cell cytoplasm. PHB is thermoplastic and has a high degree of crystalinity and a well-defined melt temperature of about 180° C. Unfortunately, PHB becomes unstable and degrades at elevated temperatures near its melt temperature. Due to this thermal instability, commercial applications of PEB have been extremely limited.

Other polyhydroxyalkanoates, such as poly(3-hydroxybutyrate-co-3-hydroxybutyrate) (PHBV), have also been investigated. Examples of PHB homopolymer and PHBV copolymers are described in the Holmes et al. U.S. Pat. Nos. 4,393,167 and 4,880,59, and PHBV copolymers are commercially available from Monsanto under the trade name BIOPOL. Unfortunately, polyhydroxyalkanoates such as PHB and PHBV are difficult to process into films for use in various applications. As previously discussed, the thermal instability of PHB makes such processing nearly impossible. Furthermore, the slow crystallization rates and flow properties of PHB and PHBV make film processing difficult. PHBV copolymers are typically produced with valerate contents ranging from about 5 to about 24 mol %. Increasing valerate content decreases the melt temperature of the polymer. However, owing to the relatively small changes in crystallinity, PHBV films often remain stiff and brittle for many applications Improved biodegradable copolymers are disclosed by Noda, for example in U.S. Pat. Nos. 5,498,692, 5,536,564, 5,602,227 and 5,685,756. The biodegradable copolymers of Noda comprise at least two randomly repeating monomer units (RRMUIs), wherein the first RRMU has the structure [—O—CH($R^1$)—($CH_2$)$_n$—C(O)—] wherein $R^1$ is H or C1 or C2 alkyl, and n is 1 or 2, and the second RRMU has the structure [—OCH($R^2$)—$CH_2$—C(O)—] wherein $R^2$ is a C4-C19 alkyl or alkenyl, and wherein at least 50% of the RRMUs have the structure of the first RRMU. These copolymers are advantageous in that they are biodegradable and exhibit a good combination of physical properties which allow their processing into films, sheets, fibers, foams, molded articles, nonwoven fabrics and the like to provide a variety of useful articles. However, these copolymers are not soft and elastic, while maintaining strength when they are in their original unstretched state.

Polyhydroxyalkanoate (PHA) copolymers consisting essentially of the repeat units having relatively long alkyl pendant groups of three to nine carbons, such as polyhydroxyalkanoate, are known to exhibit soft and rubber-like elasticity with some level of strength. (See for example, K. D. Gagnon, R. W. Lenz, R. J. Farris, and R C. Fuller, Macromolecules, vol. 25, pp.3723–3728, 1992.) The utility of soft and elastic products made of such PHA copolymers, however, is severely limited by the disappointingly low melt temperature around 60° C. The dimensional stability of the product is compromised even at a temperature of a warehouse in summer which can reach above 80° C. Thus, a biodegradable soft and elastic product made of polymers having a higher melt temperature range is desired.

It is often desirable to stretch thermoplastic polymers in order to alter their physical properties. Unfortunately, PHB and PHBV form brittle products that typically break even when drawn to only a very small extent. Various methods have been attempted to improve the stretching processes and the resulting properties of stretched or drawn PHB and PHBV products, for example as disclosed in the Holmes U.S. Pat. No. 4,537,738 and the Barham et al U.S. Pat. No. 4,427,614. Additional methods are disclosed in the Safta European Reference EP 736,563 A1, the Institute of Physical and Chemical Research European Reference EP 849,311 A2, the Waldock WO reference 97/22459, Kusaka et al *Pure Appl. Chem.*, 834(2):319–335 (1998) and Yamamoto et al, *Intern. Polymer Processing* XII, (1997) 1:29–37. However, such methods have not been particularly successful in providing means for easily forming stretched products having a certain combination of desired physical properties. In particular, the prior art does not provide polymer products having softness and elasticity, while maintaining strength.

Accordingly, it would be advantageous to obtain polymer products which are biodegradable and which have a desirable combination of soft and elastic properties allowing use of the products in a wide range of applications.

SUMMARY OF THE INVENTION

Accordingly, it is an object of the present invention to provide new products and methods which overcome disadvantages of the prior art. It is a related object of the present invention to provide polymer products formed of compositions comprising a biodegradable polymer. It is a further object of the invention to provide polymer products which exhibit advantageous combinations of physical properties. It is a more specific object of the invention to provide biodegradable polymer products which exhibit softness and elasticity while maintaining strength. It is another object of the invention to provide methods for easily forming such products. It is yet a further object of the invention to provide articles comprising such polymer products.

These and additional objects and advantages are provided by the products and methods of the present invention. In one embodiment, the invention is directed to polymer products which are obtained by stretching a composition comprising a biodegradable polyhydroxyalkanoate copolymer. The biodegradable polyhydroxyalkanoate copolymer comprises at least two randomly repeating monomer units (RRMUs). The first RRMU has the structure (I):

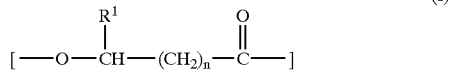

wherein $R^1$ is H, or C1 or C2 alkyl and n is 1 or 2. The second RRMU has the structure (II):

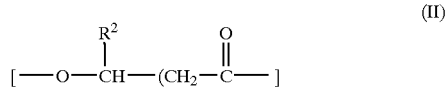

wherein $R^2$ is a C3–C19 alkyl or C3–C19 alkenyl.

Optionally, the copolymer further comprises a third randomly repeating unit having the structure (III):

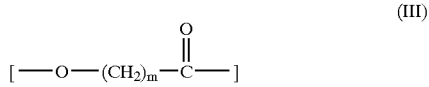

wherein m is from 2 to about 9. At least about 70 mole % of the copolymer comprises RRMUs having the structure of the first RRMU of formula (I) Suitable polymer products include, but are not limited to, films, sheets, fibers, nonwovens, and products formed by bonding a plurality of fibers, for example nonwoven sheets and the like. The polymer products of the invention are advantageous in that they exhibit a combination of softness and elasticity while maintaining strength.

In another embodiment, the invention is directed to methods of forming improved biodegradable polymer products. The methods comprise stretching a composition comprising a biodegradable polyhydroxyalkanoate copolymer at a temperature above the glass transition temperature $T_g$ of the composition and below the melting temperature $T_m$ of the composition. The biodegradable polyhydroxyalkanoate copolymer comprises at least two RRMUs, wherein the first RRMU has the structure of formula (I) and the second RRMU has the formula (II) as defined above. Optionally, the copolymer further comprises a third RRMU, wherein the third RRMU is different from the first RRMU and has the structure of formula (III), as defined above. At least about 70 mole % of the copolymer comprises RRMUs having the structure of the first RRMU of formula (I).

Conveniently, conventional solid state stretching may be employed. Thus, the methods of the invention comprise relatively easy steps as compared with many of the cumbersome methods of the prior art for producing stretched polymer products, and provide stretched polymer products having an advantageous combination of physical properties.

These and additional objects and advantages will be more fully understood in view of the following detailed description.

DETAILED DESCRIPTION

While not intending to be bound by theory, it is believed that the stretching process, to some degree, orients the copolymer chains of the products according to the invention. The stretched polymer products of the invention unexpectedly exhibit an advantageous combination of physical properties, and particularly exhibit softness and elasticity while maintaining strength. Particularly, the stretched polymer products of the invention exhibit both a higher strength, for example as measured by a higher tensile stress at break, and a higher softness, for example as measured by a lower tensile modulus, as compared with an unstretched product of the same composition. This combination of properties is a highly unexpected outcome of a stretching process. Typically, a stretching process results in products that are both stronger and stiffer (less soft), not stronger and softer. For example, for fibers, M. S. M. Mark describes in *Polymer Science Dictionary*, Elsevier Applied Science, New York (1989), page 295, that "drawn or spun fibres are deliberately oriented along their length to enhance strength and stiffness in this direction due to uniaxial orientation", and L. E. Nielson and R. F. Landel describe in *Mechanical Properties of Polymers and Composites*, 2$^{nd}$ Edition, Marcel Dekker, Inc., New York (1994), page 116 that "many highly oriented fibers have Young's moduli about an order of magnitude greater than that of the unoriented polymers". For films, Nielson and Landel (page 116) also describe that "Biaxially oriented firms, made by stretching in two mutually perpendicular directions, have reduced creep and stress relaxation compared to unoriented materials. Part of the effect is due to the increased modulus."

The products exhibit good elasticity in that they are able to recover quickly when a deforming force or pressure is removed. In preferred embodiments, the elasticity exhibited by the present products is springy in that the products easily respond to an applied stress and quickly return to their original shape after release of the deforming stress. This springy behavior which is exhibited by preferred products according to the invention may be similar to the elasticity of vulcanized rubber and certain synthetic thermoplastic elastomers. However, the present products also exhibit high strength and resistance to creep, whereby the products resist premature deformation at low stress and resist sagging when used. The products of the invention also exhibit good softness in that they can be bent, twisted or folded without breaking. In preferred embodiments, the softness is accompanied by a supple quality which allows the materials to be readily bent, twisted or folded without any sign of injury. Thus, the present products are able to exhibit high strength at large deformations that is generally exceeded only by highly oriented materials, while exhibiting supple and springy characteristics at small deformations which provide enhanced pliability or drape, i.e., the products more easily conform to and fit more snugly around objects. Additionally, the products do not exhibit tackiness which is associated with many conventional elastomers without the use of powders or other antiblock agents that may affect performance or interact negatively in a desired application. Importantly, the present products are biodegradable.

The stretched polymer products are formed from a composition comprising a biodegradable polyhydroxyalkanoate copolymer comprising at least two RRMUs. The first RRMU has the structure (I):

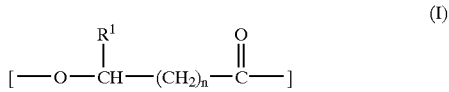

wherein $R^1$ is H, or C1 or C2 alkyl, and n is 1 or 2. In a preferred embodiment, $R^1$ is a methyl group ($CH_3$), whereby the first RRMU has the structure:

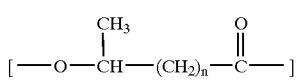

wherein n is 1 or 2. In a further preferred embodiment of the first RRMU, $R^1$ is methyl and n is 1, whereby the polyhydroxyalkanoate copolymer comprises 3-hydroxybutyrate units.

The second RRMU included in the biodegradable polyhydroxyalkanoate copolymer has the structure (II):

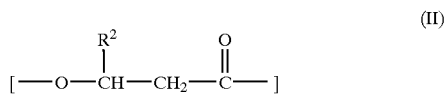

wherein $R^2$ is a C3–C19 alkyl or C3–C19 alkenyl. Generally, in the RRMU of formula (II), the length of $R^2$ will, to some extent, influence the reduction in overall crystallinity of the copolymer. In a preferred embodiment, $R^2$ is a C3–C15 alkyl group or alkenyl group. In a further preferred embodiment, $R^2$ is a C3–C9 alkyl group, and in a further preferred embodiment, $R^2$ is a C5 alkyl group. In alternately preferred embodiments, $R^2$ is a C15–C19 alkyl or alkenyl group.

Optionally, the biodegradable polyhydroxyalkanoate copolymer may comprise a third RRMU having the structure (III):

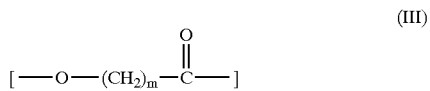

wherein m is from 2 to about 9, wherein the third RRMU is different from the first RRMU. Preferably m is from about 2 to about 5, more preferably m is about 3.

In order to obtain the advantageous combination of physical properties exhibited by the stretched polymer products of the present invention while maintaining the biodegradability of the polyhydroxyalkanoate copolymer, at least about 70 mole % of the copolymer comprises RRMUs having the structure of the first RRMU of formula (I). Suitably, the molar ratio of the first RRMUs to the second RRMU in the copolymer is in the range of from about 70:30 to about 98:2. More preferably, the molar ratio is in the range of from about 75:25 to about 95:5, and even more preferred, the mole ratio is in the range of from about 80:20 to about 90:10. As a result, the polyhydroxyalkanoate copolymer suitably has a number average molecular weight of greater than about 150,000 g/mole. While not intending to be bound by theory, it is believed that the combination of the second RRMU's side chain $R^2$ and the indicated molar amounts sufficiently decrease the crystallinity of the first RRMU to form the copolymer with desired physical properties.

In further embodiments of the polyhydroxyalkanoate copolymer employed in the compositions, one or more additional RRMUs may be included. Suitably, the additional RRMUs may have the structure

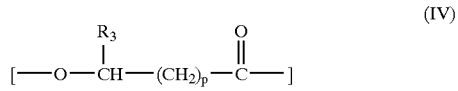

wherein $R^3$ is H, or a C1–C19 alkyl or alkenyl group and p is 1 or 2, with the provision that the additional RRMUs are not the same as the first, second or third RRMUs.

The biodegradable polyhydroxyalkanoate copolymers can be synthesized by chemical or biological based methods as disclosed, for example, by Noda in U.S. Pat. No. 5,618,855, and Noda et al. in U.S. Pat. No. 5,942,597, both of which are incorporated herein by reference.

The compositions preferably comprise greater than about 50 weight percent of the biodegradable polyhydroxyalkanoate copolymer, and it is preferred that the copolymer is present as a continuous phase in the composition. In one embodiment, the composition may comprise the polyhydroxyalkanoate copolymer as the only polymeric component, while in yet other embodiments, one or more additional polymers or copolymers may be included in combination with the polyhydroxyalkanoate copolymer. For example, the compositions may include a combination of two or more of such biodegradable polyhydroxyalkanoate copolymers, a combination of the biodegradable polyhydroxyalkanoate copolymer as defined herein, and other polyhydroxyalkanoate copolymers, and/or additional polymeric components, for example additional polyester components or the like. In such embodiments, the biodegradable polyhydroxyalkanoate copolymer preferably comprises at least about 50 weight percent, more preferably at least about 60 weight percent, and even more preferably at least about 75 weight percent, of the composition.

The compositions may further include various nonpolymeric components including, among others, nucleating agents, antiblock agents, antistatic agents, slip agents, pro-heat stabilizers, antioxidants, pro-oxidant additives, pigments, fillers and the like. These additives may be employed in conventional amounts although, typically, such additives are not required in the composition in order to obtain the advantageous combination of softness, elasticity, and strength. Additionally, one or more plasticizers may be employed in the compositions in conventional amounts although again, plasticizer are typically not required in order to obtain the advantageous combination of properties discussed above.

The upper limit of the use temperature of biodegradable polymer products, which exhibit a desirable combination of softness and elasticity, while maintaining strength, may be substantially higher than room temperature, because of the relatively high melt temperature of the polymer used to fabricate such products. Preferably the upper limit of the use temperature of the products can exceed above 80° C. without melting or becoming excessively soft, more preferably above 100° C., even more preferably above 120° C.

The polymer products may be in any physical form and typically will comprise a stretched film, sheet, fiber, or nonwoven or a product from a stretched film, sheet, fiber, or nonwoven. For example, a stretched nonwoven product can be produced by stretching a nonwoven structure that has been made by conventional means including spunbonding, melt blowing, air-laying, carding, hydroentangling, or combinations of the forementioned and the like, and in which the nonwoven can be bonded by any means known in the art, including but not limited to thermal, mechanical, chemical, or adhesive bonding. Alternatively, a plurality of stretched fibers can be bonded to form a nonwoven web which can exhibit similar softness, elastic and strength properties to the previous approach. Additionally, the stretched polymer product need not be limited to single component structures, for example, monolayer film or monofilament fibers. The stretched polymer products can also include various multi-constituent products, including but not limited to (1) fiber or nonwovens having side-side, sheath-core, multiple-segment, islands-in-the-sea, and matrix-fibril morphologies, (2) coextruded films or sheets consisting or two or more layers, (3) film/fiber, sheet/fiber, film/nonwoven, or sheet/nonwoven composites, or (4) combinations of 1–3, as long as the PHA copolymer(s) comprise at least 50 weight percent of the composition, more preferably at least about 60 weight percent, and even more preferably at least about 75 weight percent. Further, one skilled in the art will appreciate that the level of elasticity, strength, and softness exhibited by a stretched multiconstituent polymer product will be influenced by the particular morphology and configuration, such as described in part in *Polymer Blends and Alloys*, M. J. Folkes and P. S. Hope (Editors), Chapman & Hall, New York (1993), and in *Plastics Films*. $2^{nd}$ Edition, J. H. Briston, Longman Inc., New York (1983).

The stretched polymer products may be conveniently formed by conventional solid state stretching techniques wherein the composition is stretched at a temperature above the glass transition temperature $T_g$ of the composition and below the melting temperature $T_m$ of the composition. Preferably, the product is obtained by solid state stretching the composition at a temperature at least 20° C. above the glass transition temperature ($T_g$+20° C.) and at least 20° C. below the melting temperature ($T_m$–20° C.) of the composition. The glass transition temperature of the polyhydroxyalkanoate copolymers employed in the compositions of the invention are generally below room temperature, i.e., less than about 25° C. Generally, the melting temperatures of the copolymers are greater than about 100° C.

One skilled in the art will appreciate that the level of elasticity, including the springy characteristics, strength and softness exhibited by the stretched product will be influenced by not only the stretching temperature, but also by the rate and extent of stretching, whether the stretching is carried out at a constant or variable rate of displacement, strain or stress, the type of stretching and, for films, sheets, or nonwovens, whether the stretching is uniaxial or biaxial and, if biaxial, whether the stretching steps are performed sequentially, simultaneously, or some combination thereof. The stretching may be conducted at a constant or variable rate of displacement, strain or stress in accordance with techniques known in the art, for example, by a tenter framing process for films, sheets, and nonwovens, such as described by J. H. Briston in *Plastics Films*, $2^{nd}$ Edition, Longman Inc., New York (1983), pages 83–85, or for fiber products by a spinning operation with Godet rolls or filament winding, such as described by J. E. McIntyre and M. J. Denton in *Concise Encyclopedia of Polymer Science and Engineering*, John Wiley & Sons, New York (1990) pages 390, 391, and 395. Additionally, for films, sheets, and nonwovens, the stretching may be performed uniformly across the form, for example as achieved in a tenter framing process, or incrementally across the form, for example as in a, ring-rolling operation such as described in U.S. Pat. Nos. 4,116,892 and 5,296,184 where alternating parallel regions that are stretched coexist with with regions that remain virtually unstretched. Additionally, for blown films and sheets, the stretching can be performed by the double or tubular bubble process, such as described by J. H. Briston in *Plastics Films*, $2^{nd}$ Edition, Longman Inc., New York (1983), page 85. Further, depending upon the end use, the stretching of films, sheets, and nonwovens may be performed uniaxially or biaxially, and, if biaxially, the stretching steps may be performed sequentially, simultaneously or any combination thereof, in accordance with techniques known in the art. All of the above described methods of stretching films, sheets, and nonwovens, including uniform as well as incremental stretching processes, can be used and are within the scope of the present invention.

The extent of stretching must exceed the yield or neck point in at least one direction of stretch while remaining below the failure point in all stretch directions. Preferably, the product is obtained by stretching the composition in at least one direction to an extent greater than about 50% strain from its initial unstretched state, and more preferably in at least one direction greater than about 100% strain from its initial unstretched state. In further preferred embodiments, the product is obtained by stretching the composition in at least one direction to an extent in the range from about 200% to, about 1500% strain from its initial unstretched state, and more preferably in at least one direction in the range from about 300% to about 1000% strain from its initial unstretched state. Additionally, one skilled in the art will further appreciate that the effective strain in each stretch direction will depend on the deformation process and geometry. For example, in a uniform stretching process like fiber spinning the effective strain is determined by the drawdown ratio, which is the ratio of the velocity of the fiber exiting the Godet or stretching rolls divided by the velocity of the fiber entering the Godet or stretching rolls, and as such is proportional to the overall change in sample length. By contrast, for example, in an incremental stretching process like ring rolling the effective strain is determined by the draw ratio within each stretch or gauge section such as disclosed in U.S. Pat. No. 4,116,892 referenced above, and as such is proportional to localized changes in length within each stretch region and not generally to the overall change in sample length.

Generally, once the stretching has been completed, the stretched polymer product may be cooled to below its glass transition temperature or may be subjected to a heat-setting step where the stretched form is annealed under strain at a temperature above the glass transition temperature of the composition but below the melting temperature of the composition and typically in the range of from about $T_g$+20° C. to about $T_m$–20° C.

The solid state stretching may be conducted using any suitable apparatus known in the art, such as discussed above. The examples set forth below describe the use of an Instron universal testing machine, but one of ordinary skill will appreciate other apparatus which may be employed. The Instron or other stretching apparatus which is employed is preferably equipped with an environmental chamber to provide a thermally controlled stretching process. One skilled in the art will appreciate that the stretching conditions and the annealing conditions, if employed, can be determined for a given composition as described herein depending on the desired end use application.

The stretched products of the present invention are advantageous in exhibiting a good combination of softness and elasticity while maintaining strength. More specifically, the stretched polymer products of the invention exhibit (1) higher strength, for example as measured by a higher tensile stress at break, (2) higher softness, for example as measured by a lower Young's modulus, and (3) higher elasticity, for example as measured by a higher percent recovery after release of the deforming stress, as compared with, an unstretched product of the same composition. In preferred embodiments, the stretched, polymer products have a tensile strength of greater than about 15 MPa, as measured for example according to ASTM D882-97 for films, and preferably greater than about 20 MPa. Additionally, in preferred embodiments, the stretched polymer products have a Young's modulus of less than about 400 MPa, as measured for example according to ASTM D882-97 for films, more preferably less than about 300 MPa, and even more preferably less than about 200 MPa.

The elasticity of the stretched products, and particularly the springiness of the products, allows the products to substantially recover when the stretched products are elongated, for example during use. Thus, in a preferred embodiment, the stretched polymer products exhibit elastic behavior that results in greater than about 65% recovery of the product in less than about 15 seconds when the product is elongated up to about 50%, as measured for example according to ASTM D5459-95 for films. More preferably greater than about 75% recovery, and even more preferably greater than about 85% recovery.

The stretched products are useful for comprising various biodegradable articles including disposable, environmentally benign packaging, overwrap, absorbent articles including diaper/catemenial/feminine hygiene topsheets, nonwoven cores, and backsheets, stretch films including food and pallet wrap, agricultural films, mulch film, balloons, skin packaging, stretch packaging, bags including food and garbage bags, contraceptives including condoms and diaphraghms, shrink packaging, synthetic paper, carpeting, fishing line, hospital gowns, gloves, band-aids, wound dressings, disposable garments including shirts and socks, disposable surgical drapes, sutures, mailing envelopes, and agricultural uses including row covers, bed covers, turf covers, and weed barriers.

The products and methods of the present invention are further exemplified in the following examples. In the examples and throughout the present specification, parts and percentages are by weight unless otherwise specified.

EXAMPLE 1

This example demonstrates uniaxial stretching of a melt extrusion cast film according to the invention. Specifically, a copolymer of 3-hydroxybutyrate and 8.4 mole percent 3-hydroxyoctanoate (hereafter a PHBO copolymer) is melt extruded into cast films of varying thicknesses ranging from about 0.003 to about 0.004 inches. Rectangular strips of about 1×4 inches are cut from the film with the long dimension parallel to the machine direction of fabrication. Individual strips are placed in an Instron universal testing machine (Model 1122, Canton, Mass.) such that the long dimension is in the pull direction, with a test gage length of one inch. The test machine is equipped with a Sintech ReNew™ 1122/R upgrade package, TestWorks™ V3.02 software for test control and analysis, and 200 lbs high/low temperature pneumatic grips (model S512.01), all from MTS Systems Corp., Research Triangle Park, N.C., as well as an environmental chamber, Series 3710, from MTS Direct, Eden Prairie, Minn., to provide thermally controlled uniaxial stretching. For tests in which the stretching temperature is different from ambient, the test strips are allowed to equilibrate for about 2–3 minutes before starting the stretching process. Film strips of the PHBO cast film can be extended beyond 1500% elongation before failure. In addition, the stretched strips exhibit elastic behavior, i.e., when clamped between the thumb and forefinger on each hand of a technician and then pulled apart, the film is easily extended and quickly returns to its original length after release. This behavior demonstrates that the PHBO film composition is highly ductile and the stretched PHBO film composition is springy.

EXAMPLE 2

This Example demonstrates uniaxial stretching of a PHBO copolymer melt spun fiber according to the invention. The PHBO copolymer from Example 1 is melt spun into fibers having a diameter of about 4 mm. Test strands about 3 inches long are cut from the PHBO fiber. Following the stretching procedure described in Example 1, using a stretching temperature of about 60° C. and an initial strain rate of about 2 in/in-min, strands of the PHBO fiber can be elongated in excess of 1000% before failure. In addition, the stretched fiber strands exhibit an elastic behavior, i.e., when clamped between the thumb and forefinger on each hand of a technician and then pulled apart, the fiber is easily extended and quickly returns to its original length after release. This behavior demonstrates that the PHBO fiber composition is highly ductile and the stretched PHBO fiber is springy.

EXAMPLE 3

This Example demonstrates uniaxial stretching of a comparative melt extension cast film. A copolymer of 3-hydroxybutyrate and 12 mole percent 3-hydroxybutyrate (hereinafter PHBV copolymer) obtained from Zeneca Bioproducts Inc. (New Castle, Del.) is melt extruded into a cast film having a thickness of about 0.003 inches. Following the sample preparation and stretching procedure described in Example 1 for various stretch temperatures and initial strain rates, the PHBV film strips do not stretch past 10% elongation without breaking. This behavior demonstrates that PHBV compositions are stiff and brittle, and generally do not form stretched polymer products.

EXAMPLE 4

This Example demonstrates uniaxial stretching of a melt extrusion cast film according to the invention. A copolymer of 3-hydroxybutyrate and 6.9 mole percent 3-hydroxyhexanoate (hereafter a PHBH copolymer) is melt extruded into a cast film having a thickness of about 0.002 inches. Following the sample preparation and stretching procedure described in Example 1, using a stretching temperature of about 60° C. and an initial strain rate of about 4 in/in-min, film strips of the PHBH cast film can be extended beyond 400% elongation before failure. In addition, the stretched strips exhibit an elastic behavior, i.e., when clamped between the thumb and forefinger on each hand of a technician and then pulled apart, the film is easily extended to 1.5 times its original length and quickly returns to its original length after release. This behavior demonstrates the PHBH composition is ductile and the stretched PHBH film composition is springy.

EXAMPLE 5

This Example demonstrates uniaxial stretching of another melt extrusion cast film according to the invention. A copolymer of 3-hydroxybutyrate and 9.7 mole percent 3-hydroxyoctadecanoate (hereafter a PHBOd copolymer) is melt extruded into cast films of varying thicknesses ranging from about 0.002 to about 0.005 inches. Following the sample preparation and stretching procedure described in Example 1, using a stretching temperature of about 60° C. and an initial strain rate of about 60 in/in-min, film strips of PHBOd cast film can be extended beyond 1000% elongation before failure. In addition, the stretched strips exhibit an elastic behavior, i.e., when clamped between the thumb and forefinger on each hand of a technician and then pulled apart, the film is easily extended to 1.5 times its original length and quickly returns to its original length after release. This behavior demonstrates that the PHBOd composition is highly ductile and the stretched PHBOd film composition is springy.

EXAMPLE 6

This Example demonstrates biaxial stretching of a PHBO melt extrusion cast film according to the invention. A film strip of the PHBO copolymer cast film from Example 1 is first stretched about 300% according to the procedure described in Example 1 at a temperature of about 60° C. and an initial strain rate of about 4 in/in-min. This stretched sample is then rotated ninety degrees within the test machine such that the first stretch direction is perpendicular to the pull direction. A second stretch of about 300% elongation is carried out a temperature of about 60° C. and an initial strain rate of about 4 in/in-min. The springy nature of the resulting biaxially oriented film is readily discerned by simply stretching the film by hand, as the film quickly returns to its original length after release of the deforming strain.

EXAMPLE 7

This Example compares tensile properties of stretched and unstretched PHBO melt extrusion cast films. Specifically, the tensile properties of stretched and unstretched PHBO melt extruded cast film strips from Example 1 are determined by a method outlined in ASTM D882-97 using an Instron universal testing machine such as described in Example 1. The stretched samples are produced at a stretch temperature of about 60° C. and an initial strain rate of about 100 in/in-min. The stretched films are stronger, as evidenced by a higher stress at break, softer, as evidenced by a lower Young's modulus, but less extensible, as evidenced by a lower strain at break, than the unstretched counterparts.

EXAMPLE 8

This Example demonstrates the elastic recovery of a stretched PHBO melt extrusion cast film according to the invention. The elastic properties of a stretched PHBO cast film from Example 1 are measured by determining the dimensional recovery exhibited by a film when it is stretched in an Instron universal testing machine, such as described in Example 1. The stretched films are prepared at a stretch temperature of about 60° C. and an initial strain rate of about 100 in/in-min. The stretched films are extended at ambient temperature to a predetermined extension at an initial strain rate of 1.0 in/in-min, the applied stress removed, and the decrease in strain measured after about 10–15 seconds relaxation time. The stretched PHBO film strips show a short-term recovery of greater than about 85% from up to about 100% extension. This behavior demonstrates the long-range mechanical elasticity of the products according to the invention

EXAMPLE 9

This Example demonstrates an elastic, pliable band-aid formed from stretched PHBO cast film according to the invention. A stretched film is prepared from a PHBO cast film of Example 1, where the stretching process is carried out at a temperature of about 60° C. and an initial strain rate of about 20 in/in-min. A 0.75×3 inch film strip is cut from the stretched PHBO film. An absorbent pad 0.75×1.0 inch is glued lengthwise to the center of the strip, and self-adhering Velcro pieces are attached to the ends to form a band-aid. Use of the band-aid on an index finger shows that the film easily flexes, and follows both the back-and-forth and bending motions of the index finger without sagging.

EXAMPLE 10

This Example demonstrates the fabrication of a springy, soft nonwoven sheet from stretched PHBO fiber according to the present invention. A nonwoven sheet is prepared from stretched PHBO fibers. Melt spun PHBO fibers are stretched as described in Example 2 at a temperature of about 60° C. and an initial strain rate of about 3.0 in/in-min. Several of the stretched strands are cut to 3 inch lengths and placed randomly between two 10 mm think, 6×6 inch sheets of polytetrafluoroethylene (Teflon®), the whole being placed between the platens of a Carver® hydraulic laboratory press. The upper platen is preheated to about 15° C. above the calorimetrically determined melting point of the PHBO, and has a equally spaced spot bonding pattern of 25 1.0 mm diameter bonds per square inch. Sufficient pressure is applied so as to cause the bond spots to soften and fuse. The pressure is released and the nonwoven sheet is allowed to cool to room temperature before removing the outer polytetrafluoroethylene sheets. The springy nature of the nonwoven sheet is readily discerned by simply stretching the sheet by hand, as the sheet quickly returns to its original dimensions after release of the applied strain.

EXAMPLE 11

The Example demonstrates uniaxial stretching of conventional melt extrusion cast films and tensile properties thereof. Melt extruded cast films are made from several biodegradable polymers including polycaprolactone (Tone® P787, Union Carbide,), Bionolle 1001 and 3001 (Showa Highpolymer Co., LTD., Tokyo, JP), Eastar 14766 (Eastman Chemical Company, Kingsport, Tenn.), and BAK 1095 (Bayer Corporation, Pittsburgh, Pa.), as well as from several nondegradable polymers including polypropylene (type 7300KF, Millennium Petrochemicals, Cincinnati, Ohio), high density polyethylene (HDPE) (type LTPR059, Millennium Petrochemicals, Cincinnati, Ohio), and a 50:50 by weight low density polyethylene (LDPE):linear low density polyethylene (LLDPE) blend (type NA940000 and GA5010110, respectively, Millennium Petrochemicals, Cincinnati, Ohio). Following the sample preparation and stretching procedure described in Example 1, using a stretching temperature of about 25° C. and an initial strain rate of about 1.0 in/in-min, film strips of various cast films can be extended beyond 300% elongation before failure. This behavior is consistent with film compositions that are ductile.

The tensile properties of the stretched melt extruded cast film strips are determined by the method outlined in ASTM 882-97 using an Instron universal testing machine such as described in Example 1. Typical of stretching processes, the various stretched films are stronger, as evidenced by higher stress at break, but stiffer, as evidenced by higher Young's modulus, and less extensible, as evidenced by lower stress at break, than the unstretched counterparts.

Comparing the tensile properties of the stretched PHBO films from Example 7 with the tensile properties of the stretched films from this Example shows that the PHBO films are softer than the stretched films formed from the conventional compositions. In fact, the stretching process enhances the softness of the PHBO films, as evidenced by a decrease in the Young's modulus, whereas the conventional compositions all show an increase in stiffness as evidenced by an increase in Young's modulus. In all cases, the stretched films show some level of recovery from small extensional deformations; however, it becomes much harder to extend the stretched films formed from the conventional compositions beyond relatively low elongations, compared with a stretched film according to the invention. For example, a 10 lb stretching force, or equivalently a 35 MPA stress for a one inch wide film strip 0.002 inches thick, results in an immediate 50% extension for a stretched PHBO film, whereas, the stretched films formed from the conventional compositions at best show an immediate 8% extension.

EXAMPLE 12

This example demonstrates the fabrication of a nonwoven sheet using a melt blown process. The PHBO copolymer from Example 1 is fed into an extruder which gradually melts the polymer as it feeds the melt blowing die. The die meters the polymer into a balancing channel that is oriented linearly in the cross machine direction and that narrows to a spinneret of several holes per linear inch. At the point of exit the polymer strands are attentuated by heated, high velocity air. The fibers that are formed are continuous and extremely fine, and are blown onto a moving collector screen to form the nonwoven web structure. The web is thermally bonded by passing the web through a 2-roll stainless steel stack roll on which one roll there is a spot bonding pattern of about 25 1.0 mm diameter bonds per square inch. The stack rolls are preheated to about 15° C. above the calorimetrically determined melting point of the PHBO composition, and sufficient pressure is applied to the web as it passes through the stack roll so as to cause the spot bonds to soften and fuse. The lack of elasticity is readily discerned by simply stretching the nonwoven web by hand, as the web does not easily elongate and does not return to its original dimensions after release of the applied strain.

EXAMPLE 13

This example demonstrates the fabrication of a springy nonwoven sheet from a melt blown nonwoven web. Rectangular strips of about 1×4 inches are cut from the bonded PHBO web described in Example 12, with the long dimension parallel to the machine direction of fabrication. Following the stretching procedure described in Example 1, using a stretching temperature of about 60° C. and an initial strain rate of about 1 in/in-min, elongated strips of the PHBO nonwoven web can be produced. The springy nature of the stretched nonwoven sheet is readily discerned by simply stretching the sheet by hand, as the sheet is easily elongated and quickly returns to it original dimensions after release of the applied strain. Comparing this behavior with that of Example 10 shows that similar springy nonwoven products can be produced by either stretching a nonwoven sheet made by conventional means or by fabricating a nonwoven sheet from stretched fibers.

EXAMPLE 14

This example demonstrates the fabrication of a springy film product by incrementally stretching a PHBO film in a ring rolling operation according to U.S. Pat. No. 4,116,892. The melt extruded PHBO cast film from Example 1 is introduced in the machine direction of manufacture through a pair of grooved rolls that are preheated to a temperature of about 60° C. The grooves are perpendicular to the machine direction of the film, have an approximate sinusoidal shape 3 mm deep and 3 mm apart, and produce a draw ratio of about 2. When the film is stretched to conform with the shape of the grooves, 8 groove tips simultaneously engage the film. The film is introduced into the nip of the intermeshing grooved rolls rotating at about 2 RPM to produce a feed velocity of approximately 2 feet per minute, and wound at about 4 feet per minute. The film has relatively transparent lines at 3 mm intervals corresponding to the contact points, or stretched areas, with undrawn opaque sections in between. The springy nature of the ring-rolled PHBO film is readily discerned in directions parallel to the machine direction by simply stretching the sheet by hand, as the sheet is easily elongated and quickly returns to it original dimensions after release of the applied strain. By contrast, stretching the film product in directions perpendicular to the machine direction indicates no apparent springiness or elasticity, as the sheet does not easily elongate and does not return to its original dimensions after release of the applied strain. This example illustrates that a ring rolling operation can impart a uniaxial or directional elastic behavior to a preferred film product. This approach is also applicable for preferred sheet and nonwoven products.

EXAMPLE 15

This example demonstrates the fabrication of a stretched film product by incrementally stretching a film of Bionolle 3001 (Showa Highpolymer Co., LTD., Tokyo, JP) in a ring rolling operation. Specifically, a melt extruded cast film of Bionolle 3001 with a thickness of about 0.002 inches is ring rolled according to the procedure described in Example 14, using a grooved roll temperature of about 25° C. The lack of springiness is readily discerned by simply stretching the ring rolled film product by hand in directions parallel and perpendicular to the machine direction of manufacture, as the film does not easily elongate and does not return to its original dimensions after release of the applied strain. In act, the ring rolling operation permanently deforms the Bionolle 3001 film in the machine direction.

EXAMPLE 16

This example demonstrates the fabrication of a contractive film product by incrementally stretching a multilayer film in a ring rolling operation. Specifically, the PHBO copolymer from Example 1 is coextruded with the Bionoile 3001 resin from Example 15 into a two-layer cast film product where the thickness of the PHBO layer is about 0.002 inches and the Bionolle 3001 layer is about 0.001 inches. This PHBO/Bionolle film is then ring rolled according to the procedure described in Example 14, using a grooved roll temperature of about 60° C. The result of the ring rolling operation is a contractive film product, in which the PHBO layer is springy as described in Example 14 and the Bionolle 3001 layer is nonspringy and permanently deformed as described in Example 15, and in which the Bionolle layer forms gathers or pleats as the PHBO layer contracts upon release of an applied strain. Additionally, the Bionolle layer limits the extent to which the product is rendered elastically extensible, at least up to the point of initial stretching.

EXAMPLE 17

This example demonstrates the fabrication of a disposable baby diaper, where the dimensions listed are intended for use with a child in the 6–10 kilogram size range. These dimensions can be modified proportionally for different size children, or for adult incontinence briefs, according to standard practice.

1. Backsheet: 0.020-038 mm film consisting of the PHBO copolymer from Example 1; width at top and bottom 33 cm; notched inwardly on both sides to a width-at-center of 28.5 cm; length 50.2 cm.
2. Topsheet: carded and thermally bonded staple-length polyproplyene fibers (Hercules type 151 polypropylene); width at top and bottom 33 cm; nothched inwardly on both sides to a width-at-center of 28.5 cm; length 50.2 cm.

3. Absorbent core: 28.6 g of cellulose wood pulp and 4.9 g of absorbent gelling material particles (commercial polyacrylate from Nippon Shokubai); 8.4 mm thick, calendered; width at top and bottom 28.6 cm; notched inwardly at both sides to a width-at-center of 10.2 cm; length 44.5 cm.

4. Elastic leg bands: four individual rubber strips (2 per side); width 4.77 cm; length 37 cm; thickness 0.178 mm (all the foregoing dimensions being in the relaxed state).

The diaper is prepared in standard fashion by positioning the core material covered with the topsheet on the backsheet and gluing.

The elastic bands (designated "inner" and "outer", corresponding to the bands closest to, and farthest from, the core, respectively) are stretched to ca. 50.2 cm and positioned between the topsheet/backsheet along each longitudinal side (2 bands per side) of the core. The inner bands along each side are positioned ca. 55 mm from the narrowest width of the core (measured from the inner edge of the elastic bank). This provides a spacing element along each side of the diaper comprising the flexible topsheet/backsheet material between the inner elastic and the curved edge of the core. The inner bands are glued down along their length in the stretched state. The outer bands are positioned ca. 13 mm from the inner bands, and are glued down along their length in the stretched state. The topsheet/backsheet assembly is flexible, and the glued-down bands contract to elasticize the sides of the diaper.

EXAMPLE 18

The diaper of Example 17 is modified by replacing the elastic leg bands with the springy PHBO film product described in Example 1.

EXAMPLE 19

The diaper of Example 17 is modified by replacing the elastic leg bands with the contractive film product described in Example 16.

The specific embodiments and examples set forth above are provided for illustrative purposes only and are not intended to limit the scope of the following claims. Additional embodiments of the invention and advantages provided thereby will be apparent to one of ordinary skill in the art and are within the scope of the claims.

What is claimed is:

1. A polymer product, obtained by stretching a composition characterized by a biodegradable polyhydroxyalkanoate copolymer comprising at least two randomly repeating monomer units, wherein the first randomly repeating monomer unit has the structure (I):

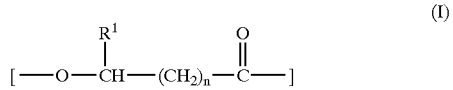

(I)

wherein $R^1$ is H, or C1 or C2 alkyl, and n is 1 or 2, and the second randomly repeating monomer unit has the structures (II):

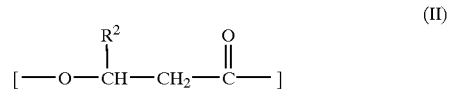

(II)

wherein R2 is a C3–C19 alkenyl, and wherein at least 70 mole % of the copolymer comprises randomly meeting monomer units having the structure of the first randomly repeating monomer unit (I);

wherein the product is obtained by stretching the composition at a temperature above the glass transition temperature $T_g$ of the composition and below the melting temperature $T_m$ of the composition.

2. A polymer product as defined in claim 1, wherein the product is obtained by stretching the composition to an extent of more than 50% strain from its initial unstretched state.

3. A polymer product as defined in claim 1, wherein the composition comprises at least 50 weight percent of the biodegradable polyhydroxyalkanoate copolymer and wherein the biodegradable polyhydroxyalainoate copolymer has a number average molecular weight of greater than 150,000 g/mole.

4. A polymer product as defined in claim 1, wherein the copolymer further comprises a third randomly repeating monomer unit having the structure (III)

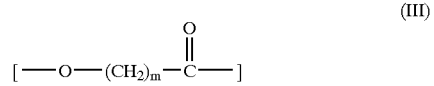

(III)

wherein m is from 2 to 9 and wherein the third randomly repeating unit is not the same as the first randomly repeating monomer unit.

5. A polymer product as defined in claim 1, wherein the product is in the form of a film.

6. A polymer product as defined in claim 5, wherein the film is uniaxially or biaxially stretched.

7. A polymer product as defined in claim 5, wherein the film is stretched by ring rolling.

8. A polymer product as defined in claim 1, wherein the product is in the form of a fiber or a nonwoven sheet.

9. A polymer product as defined in claim 1, wherein the product exhibits elastic behavior that results in at least 65% recovery of the product when the product is elongated up to 50%.

10. A polymer product as defined in claim 1, wherein the molar ratio of the first randomly repeating monomer units to the second randomly repeating monomer units in the copolymer is in the range of from about 70:30 to about 98:2.

11. A polymer product as defined in claim 10, wherein said molar ratio is, from about 75:25 to about 95:5.

12. A polymer product as defined in claim 1, wherein the product is obtained by stretching the composition at a temperature at least 20° C. above the glass transition temperature $T_g$ of the composition and at least 20° C. below the melting temperature $T_m$ of the composition.

13. A polymer product as defined in claim 1, wherein the product is obtained by stretching the composition to an extent of more than about 50% strain from its initial unstretched state.

14. A polymer product as defined in claim 12, wherein the product is obtained by stretching the composition to an extent in the range of from about 200% to about 1500% strain from its initial unstretched state.

15. A polymer product as defined in claim 14, wherein the product is obtained by stretching the composition to an extent in the range of from about 300% to about 1000% strain from its initial unstretched state.

16. A polymer product as defined in claim 12, wherein the first randomly repeating monomer unit has the structure:

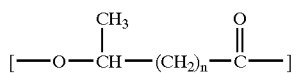

and the second randomly repeating monomer unit has the structure:

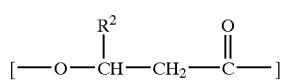

wherein $R^2$ is a C3–C19 alkyl.

17. A polymer product as defined in claim 16, wherein n is 1.

18. A polymer product as defined in claim 17, wherein $R^2$ is a C5 alkyl.

19. A polymer product as defined in claim 12, wherein the product has a higher tensile stress at break and a lower Young's modulus as compared with an unstretched product of the composition comprising the biodegradable polyhydroxyalkanoate copolymer.

20. A polymer product as defined in claim 1, wherein the product exhibits elastic behavior that results in at least about 65% recovery of the product when the product is elongated up to about 50%.

21. A polymer product as defined in claim 19, wherein the product exhibits elastic behavior that results in at least about 85% recovery of the product when the product is elongated up to about 50%.

* * * * *